US006471443B1

(12) United States Patent
Renaud (10) Patent No.: US 6,471,443 B1
(45) Date of Patent: Oct. 29, 2002

(54) METHOD AND APPARATUS FOR INJECTING STEAM INTO LANDFILLS

(76) Inventor: Regis Phillip Renaud, 28281 Silverado Canyon Rd., Silverado, CA (US) 92676-0792

( * ) Notice: Subject to any disclaimer, the term of this patent is extended or adjusted under 35 U.S.C. 154(b) by 42 days.

(21) Appl. No.: 09/838,442

(22) Filed: Apr. 19, 2001

Related U.S. Application Data (60) Provisional application No. 60/198,196, filed on Apr. 19, 2000.

(51) Int. Cl.$^7$ ................................................ B09B 5/00
(52) U.S. Cl. ........................... 405/129.95; 405/129.27; 405/129.25; 405/129.28; 210/602
(58) Field of Search ....................... 405/129.95, 129.25, 405/129.27, 129.28, 129.2; 210/603, 707, 180; 435/290.1

(56) References Cited

U.S. PATENT DOCUMENTS

| | | | | |
|---|---|---|---|---|
| 3,586,624 A | * | 6/1971 | Larson ..................... 210/195.1 |
| 4,100,023 A | * | 7/1978 | McDonald .................. 435/167 |
| 4,142,912 A | | 3/1979 | Young |
| 4,323,367 A | * | 4/1982 | Ghosh ......................... 210/603 |
| 4,334,997 A | * | 6/1982 | Peterson ..................... 210/180 |
| 4,469,176 A | * | 9/1984 | Zison et al. ................. 166/369 |
| 4,481,293 A | * | 11/1984 | Thomsen et al. ........... 435/167 |
| 4,518,399 A | * | 5/1985 | Croskell et al. ............ 210/603 |
| 4,649,741 A | * | 3/1987 | Strom ........................... 73/784 |
| 4,670,148 A | * | 6/1987 | Schneider ................... 156/250 |
| 4,798,801 A | * | 1/1989 | Hitzman ................... 435/290.1 |
| 4,845,034 A | * | 7/1989 | Menger et al. ............. 210/603 |
| 4,936,996 A | * | 6/1990 | Messing ..................... 210/603 |
| 5,139,365 A | | 8/1992 | Chesner |
| 5,238,580 A | | 8/1993 | Singhvi |
| 5,261,766 A | * | 11/1993 | Anderson .............. 405/129.35 |
| 5,265,979 A | | 11/1993 | Hansen |
| 5,362,181 A | | 11/1994 | DenBesten |
| 5,447,850 A | * | 9/1995 | McCann ..................... 435/167 |
| 5,484,231 A | * | 1/1996 | Cannan et al. .............. 166/271 |
| 5,564,862 A | | 10/1996 | Markels, Jr. |
| 5,605,417 A | | 2/1997 | Englert et al. |
| 5,695,641 A | | 12/1997 | Cosulich et al. |
| RE35,782 E | * | 5/1998 | Circeo et al. .......... 405/128.65 |
| 5,860,907 A | | 1/1999 | Kauschinger |
| 5,984,580 A | | 11/1999 | Ham et al. |
| 6,024,513 A | | 2/2000 | Hudgins et al. |
| 6,106,197 A | | 8/2000 | Kozak et al. |
| 6,299,774 B1 | * | 10/2001 | Ainsworth et al. ......... 210/178 |

OTHER PUBLICATIONS www.statigraphics.com/services.html, 8 pages, "Penetrometer soil exploration system", undated.*
ConeTec Brochures, "The Electrical Resistivity Cone" and "The Piezo Cone Penetrometer", 3 pages, undated.*

(List continued on next page.)

*Primary Examiner*—Heather Shackelford
*Assistant Examiner*—Katherine Mitchell
(74) *Attorney, Agent, or Firm*—Knobbe Martens Olson & Bear LLP (57) ABSTRACT

A method of injecting steam into a landfill is provided. The steam enhances methane gas production in the landfill during the anaerobic phase, accelerates decomposition/biodegradation of the organic component of the trash prism during both the aerobic and anaerobic phases, and increases the rate of settlement of the landfill. A method of introducing a gaseous anaerobic fertilizer into the landfill is also provided. The fertilizer accelerates the decomposition/biodegradation of the organic component of the trash prism. A method of reducing the volume of a plastic component of the trash prism is provided, wherein the temperature and pressure of injected steam are raised to a level sufficient to melt plastic. Finally, a method of reducing the volume of a quantity of refuse prior to placing the refuse in a landfill is provided, wherein the refuse is heated to melt a plastic component of the refuse.

32 Claims, 4 Drawing Sheets

OTHER PUBLICATIONS www.cerf.org/research.clusters/4–3.htm, "Non Invasive Characterization of Site Conditions", 3 pages, © 1997.* www4.ivenue.com/landfillengineering.com/ "Landfill Engineering", Steam Injection in Landfills, 16 pages total.*

* cited by examiner

Fig. 2

METHOD AND APPARATUS FOR INJECTING STEAM INTO LANDFILLS

RELATED APPLICATION

This application claims priority to provisional application Serial No. 60/198,196, filed on Apr. 19, 2000.

BACKGROUND OF THE INVENTION

1. Field of the Invention

The present invention relates to methods of treating landfills. Specifically, the invention provides a method of injecting steam into a landfill to accelerate the decomposition/biodegradation of organic refuse within the trash prism, which increases the production of methane gas, and increases the rate of settlement of the landfill. The rate of settlement of the landfill is further increased by raising the temperature therein to melt the plastic component of the refuse.

2. Description of the Related Art

In general, landfills are constructed using the "dry tomb" method, in which the refuse in the landfill is kept as dry as possible both during construction and when the landfill is closed and capped. This method minimizes the possibility of leachate leaking into groundwater and contaminating it. However, dry conditions are not conducive to the decomposition of the organic refuse. Instead, the organic refuse remains dormant for decades until water infiltrates the landfill in an uncontrolled and natural manner. The water infiltration may cause gas migration, which can lead to groundwater contamination.

The slow decomposition of the organic refuse under dry conditions also slows the settling of the landfill and hinders the production of methane gas, which is a natural by-product of anaerobic (oxygen-starved) decomposition of organic material. Delaying the complete settling of a landfill is disadvantageous, because until the landfill settles, the landfill site is not useful for any purpose other than a garbage dump. In addition, methane is useful as a fuel to produce electricity, for example. Therefore, it would be of great benefit to encourage the rapid decomposition of the organic component of the landfill in order to more efficiently capture the methane produced thereby.

Moisture accelerates decomposition of organic refuse, but does not accelerate the decomposition of the non-organic refuse. Thus, addition of moisture to the trash prism increases the purity of methane extracted from the landfill, because the proportion of decomposing organic refuse to decomposing inorganic refuse is higher as compared to a dry trash prism. The extracted methane is thus more useful because it has a higher Btu value. If the refuse is flooded with water, however, the gas becomes bound up in the liquid and is difficult to recover. Further, introducing water after a landfill has been closed cools the refuse. But decomposition proceeds best at a temperature around 100° F. Therefore, a method of introducing moisture into a trash prism that does not flood the trash prism or cool the trash prism would be of great benefit to the landfill-management industry.

One useful method of monitoring conditions within a landfill is a piezo-penetrometer test (PPT) profile. A PPT is an instrument having sensors that measure several parameters within the landfill as the instrument is hydraulically pushed into the landfill. Parameters such as soft and dense layers, vacuum, and gas and liquid pressure are recorded in a computer. This data is then used to develop a three-dimensional profile of the in-situ conditions within the landfill.

PPT profiles of landfills have shown that liquids tend to collect on top of dense and daily cover layers inside landfills, and that gases collect underneath these layers. Dense and daily cover layers are the component of the landfill that is added at the end of each day during the active phase of the landfill. The refuse deposited into the landfill each day is covered by a layer of dirt or a suitable dirt alternative. The non-uniform distribution of liquid around these layers only causes the biodegradation of the organic material in the immediate area of the liquid, rather than throughout the entire trash prism. Thus, a method of evenly distributing moisture throughout the trash prism would greatly enhance the biodegradation of the organic material in the landfill.

U.S. Pat. No. 5,695,641 to Cosulich et al., discloses a method and apparatus for enhancing methane production in a landfill. The method comprises injecting ammonia into the landfill to thereby reduce residual oxygen levels, provide a rich source of nitrogen nutrient for the anaerobic microbe population and increase the pH. The ammonia is injected via injection wells, and may be injected in any form, diluted by a non-oxidizing carrier gas or in aqueous form. The Cosulich method, however, does not suggest the benefits gained by increasing the moisture content of the landfill, or address the detrimental effects of lowering the temperature of the landfill by introducing water.

U.S. Pat. No. 6,024,513 to Hudgins et al., discloses a method of decomposing municipal solid waste (MSW) within a landfill by converting the landfill to aerobic degradation in the following manner: (1) injecting air via the landfill leachate collection system; (2) injecting air via vertical air injection wells installed within the waste mass; (3) applying leachate to the waste mass using a pressurized drip irrigation system; (4) allowing landfill gases to vent; and (5) adjusting air injection and re-circulated leachate to achieve a 40% to 60% moisture level and a temperature between 120° F. and 140° F. in steady state. One of the stated objectives of the Hudgins method, however, is to reduce the production of methane gas in the landfill. The Hudgins method thus does not provide a convenient way to produce methane for beneficial purposes.

SUMMARY OF THE INVENTION

The method of injecting steam into landfills according to this invention has several features, no single one of which is solely responsible for its desirable attributes. Without limiting the scope of this invention as expressed by the claims that follow, its more prominent features will now be discussed briefly. After considering this discussion, and particularly after reading the section entitled "Detailed Description of the Drawings," one will understand how the features of this invention provide advantages, which include minimization of the amount of liquid introduced into the landfill, total moisturization and higher overall humidity of the landfill without the need to apply head pressure, promotion of settlement of the landfill, heating of the refuse, avoidance of clogging of gas extraction collectors, ability to distribute gaseous anaerobic fertilizer throughout the trash prism, increased methane production, and production of methane having higher Btu values as compared to methane produced in other landfills.

The present method comprises injecting steam into a landfill and collecting the methane produced by the decomposition/biodegradation of the organic component of the trash prism. The steam accelerates the decomposition of the organic refuse, thereby enhancing methane gas production by increasing the purity of the methane. By accelerating the decomposition of the organic refuse, the steam also increases the rate of settlement of the landfill. The time necessary to convert the landfill into property that is useful for purposes besides waste disposal is thus reduced. The reduced decomposition time also reduces the impact of the landfill on the environment.

The steam is derived from a source such as a boiler, heat exchanger or power plant, and is injected into the landfill through an array of steam injection wells. The methane is collected through an array of gas extraction collectors distributed throughout the landfill. The wells and collectors preferably comprise steel push-in screens and risers. The optimal location for the wells and collectors is preferably determined using a piezo-penetrometer test (PPT) profile, and the wells and collectors are preferably installed in the landfill using the PPT rig. The injectors and collectors can, however, also be installed with a drill rig.

Temperature and moisture sensors are preferably distributed throughout the landfill to monitor the conditions within the landfill. Feedback from these sensors enables the amount of steam injection to be adjusted to prevent liquid from accumulating within the landfill.

In a further aspect of the present method, both air and steam are injected into the landfill in order to maintain the landfill in the aerobic phase. Injecting only air into the landfill for aerobic degradation dries out the trash prism, which slows the decomposition process and may cause subterranean fires. Thus, the moisture lost in this process must be replaced. Introducing water is disadvantageous because it cools the refuse, slowing degradation, and travels downward due to gravity. Steam, however, warms the refuse because of its high temperature. The steam, which is a vapor, also travels in all directions within the landfill just as the injected air does. Further, the air that is injected is usually cool, especially in winter. Heating the air stream will prevent the air from cooling the interior of the landfill. Steam provides this heating action.

In a further aspect of the present method, the steam serves as a carrier medium for a gaseous anaerobic fertilizer, such as ammonia or ammonia nitrate. The steam may also serve as a carrier medium for a gas, such as nitrous oxide, that speeds the conversion of the landfill from the aerobic phase to the anaerobic phase.

In a further aspect of the present method, the temperature and pressure of the injected steam are raised to a level sufficient to melt the plastic component of the trash prism, thereby promoting further settlement of the landfill. The temperature and pressure are preferably raised after substantially all of the organic component of the refuse has decomposed. After substantially all of the plastic has melted, the gas extraction collectors preferably draw off the remaining steam in order to prevent condensation within the landfill.

In a further aspect of the method, the conditions within the landfill are preferably monitored using a PPT profile. The rate of settlement, and the rate of organic decomposition provide important information about the effectiveness of the present method.

In a further aspect of the method, the volume of the plastic component of the refuse is reduced prior to placing the refuse within the landfill. The plastic is preferably melted by placing the refuse in a containerized trammel and applying high-temperature and high-pressure steam. If the plastic is to be recycled, it is preferably removed from the refuse using screens.

BRIEF DESCRIPTION OF THE DRAWINGS

The preferred embodiments of this invention, illustrating its features, will now be discussed in detail. These embodiments depict the novel and non-obvious method of injecting steam into landfills of this invention shown in the accompanying drawings, which are for illustrative purposes only. These drawings include the following figures, in which like numerals indicate like parts.

DETAILED DESCRIPTION OF THE PREFERRED EMBODIMENTS

In the present method, steam is injected into a landfill 10. The steam promotes the anaerobic biodegradation of the organic refuse in the landfill 10, which in turn increases methane gas generation and increases the rate of settlement of the landfill 10.

Figure 1:
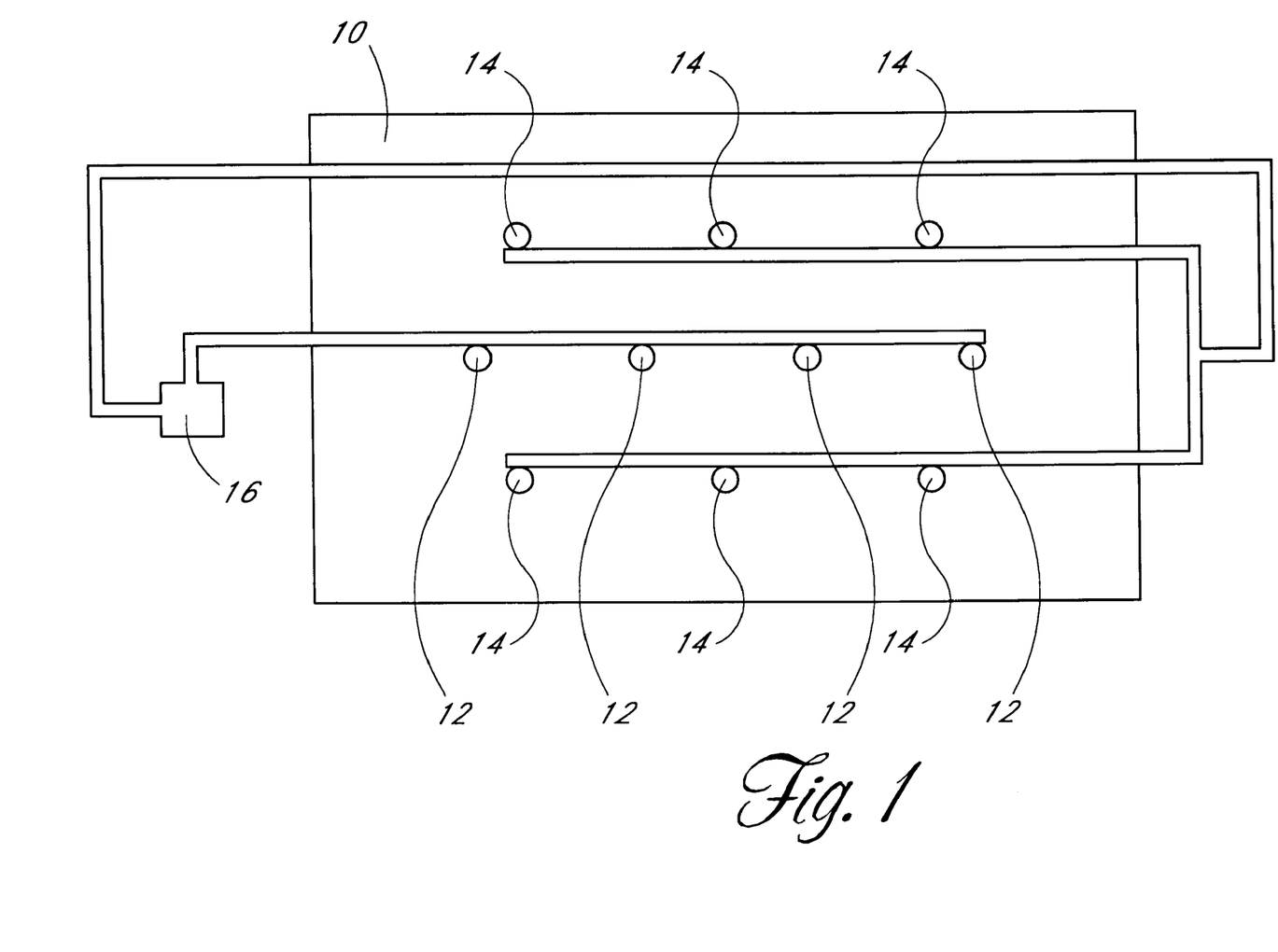
FIG. 1 is a schematic top view of an apparatus for performing one preferred embodiment of the present method.

FIG. 1 schematically illustrates an apparatus for performing the present method. Several lines of steam injection wells 12 and several lines of gas extraction collectors 14 are positioned within a landfill 10. The arrangement depicted in FIG. 1 is merely exemplary. The ideal location for the injection wells 12 and gas collectors 14 is preferably determined prior to installing the steam injection apparatus, and may differ significantly from the arrangement of FIG. 1.

One preferred method of determining the ideal location for the steam injection wells 12 and gas collectors 14 is to perform a piezo-penetrometer test (PPT) profile on the landfill 10. The PPT profile is performed with a cone-shaped instrument having sensors that measure several parameters as the cone is hydraulically pushed into the landfill 10. The PPT profile provides information about the in-situ conditions of the landfill 10. The PPT rig may also be used to install the steam injection wells 12 and gas extraction collectors 14 following the PPT profiling.

After installation of the steam injection wells 12 and gas extraction collectors 14, steam injection commences through the injection wells 12. Low pressure centers are preferably created at the gas extraction collectors 14, as by attaching a header and blower system to the collectors 14, for example. The low pressure centers create currents within the trash prism that distribute the steam throughout the trash prism. Adjustment of the relative positions of the injectors 12 and collectors 14 enables the steam currents to be altered in case particular areas of the trash prism are not receiving steam.

The source of steam 16 may be a gas-fired boiler, or a heat exchanger on the gas flare. Preferably, however, the source of steam 16 is exhaust steam from a power plant, which may be more economical to harness as compared to steam specially produced for the landfill 10.

If a portion of the landfill 10 has been flooded, the water from this portion may be used to produce steam. By submersing a heater beneath the flooded portion, the water in the landfill 10 can be boiled out and directly injected back into the drier portion of the landfill 10. This process desirably removes only the excess water and volatile organic compounds from the landfill 10. Particulates, oils and metals remain in the landfill 10.

The steam injected into the landfill 10 raises the moisture content of the landfill 10. Moisture promotes the rapid decomposition of the organic portion of the trash prism, while at the same time raising the amount of methane gas produced during decomposition. The rapid decomposition of the organic refuse causes the rapid settling of the landfill 10, which shortens the amount of time that the landfill 10 is active. Once the landfill 10 has settled a sufficient amount, it is capped, and the land may thereafter be used for other purposes.

Injecting steam into the landfill 10 is more advantageous than injecting water for a variety of reasons. First, water expands to approximately 16,000 times its original volume upon boiling. Thus, injecting steam allows total coverage of the trash prism using only a small fraction of the water that would otherwise be needed. Using less water minimizes the potential for liquid to migrate to the bottom of the landfill 10 and into the groundwater, which could cause contamination.

Second, steam, which is a vapor, is under expansion pressure. Thus, it requires no head pressure, as water does, to move it through the trash prism. Steam also moves naturally with temperature differentials, from hot to cold areas. Total coverage of the landfill 10 can thus be achieved with minimal work input to the system. The more ready expansion of steam also creates better moisture distribution and higher overall humidity as compared to water. Water tends to flow down to the bottom of the landfill 10 and stay there. The lower portion of the landfill 10 is thus humid, while the upper portions, which contain the freshest refuse, remain dry. Because methane production within the landfill 10 increases with humidity, it is advantageous to maximize the humidity throughout the trash prism, rather than raising the humidity only near the bottom of the trash prism.

Third, steam, like all gases, is compressible. Water is not. Water thus occupies free space in the landfill 10, inhibiting settlement. As stated above, the landfill 10 desirably settles rapidly. The use of steam promotes more rapid settlement of the landfill 10 than does liquid water.

Fourth, steam, which is at a higher temperature than liquid water under the same pressure, will tend to increase, rather than reduce, the overall temperature of the landfill 10. Decomposition proceeds best at about 100° F. Steam thus tends to promote better decomposition by maintaining a higher temperature within the landfill 10. The high temperature steam also tends to melt plastics within the landfill 10, further speeding the rate of settlement of the landfill 10.

Fifth, liquids carry suspended solids and calcium carbonate, which tend to clog the gas extraction collectors 14 and bottom drains of landfills. Steam does not carry suspended solids or calcium carbonates, and so will not lead to clogging.

Sixth, steam may act as a carrier for various gaseous anaerobic fertilizers, such as ammonia, ammonia nitrate and nitrous oxide. This advantage is especially important for old landfills that have been sitting dry and dormant for long periods of time. These landfills generally require additional nutrients to encourage anaerobic bacterial activity.

To achieve these and other advantages, a first preferred method of injecting steam into a landfill 10 comprises several lines of steam injection wells 12 and several lines of gas extraction collectors 14, as in FIG. 1. The injection wells and extraction collectors 14 are preferably 2" steel push-in screens and risers, but could be any diameter to suit a particular application, and could be constructed from sturdy materials other than steel. The collectors 14 preferably include sensors for measuring certain parameters, such as flow rates, methane concentrations, and Btu values, in order to monitor the effectiveness of the steam injection method. The injectors 12 and collectors 14 are also preferably installed using the PPT rig, which can push them into the landfill 10 in a fraction of the time, and at a fraction of the cost required for drilling. The injectors 12 and collectors 14 could, however, be installed with a drill rig. Another advantage of push-in injectors 12 and collectors 14 is that they can be raised and lowered at any time to ensure that they are at the optimum depth.

Figure 2:
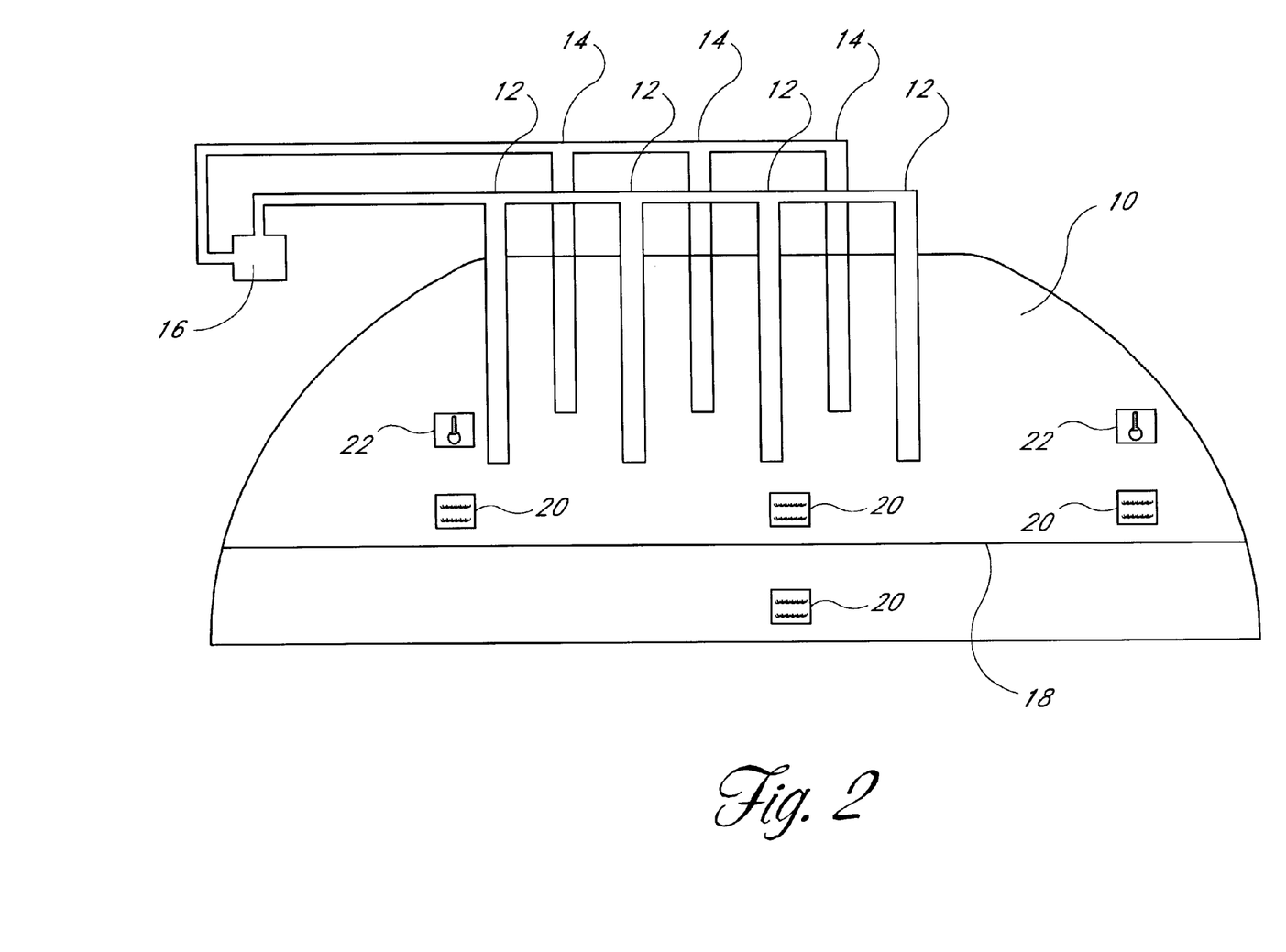
FIG. 2 is a schematic side view of the apparatus of FIG. 1.

The PPT profile preferably determines the ideal placement and spacing for the injection wells and collectors 14. The PPT profile also preferably determines the depth of the screen interval, which will be above a dense layer 18 of the landfill 10, as shown in FIG. 2. Although a variety of arrangements are workable, the gas collector screens 14 are preferably installed between the injection wells 12, and at a depth somewhat above that of the injection wells 12. In this arrangement, the gas collectors 14 draw the steam and gas upward and away from the injection wells 12. Steam injectors 12 can also be installed around gas collectors 14 that are already in place in the landfill 10.

The PPT profile also preferably determines the ideal locations of moisture sensors 20 and temperature sensors 22, shown in FIG. 2. The arrangement depicted in FIG. 2 is merely exemplary, and the actual locations for the moisture sensors 20 and temperature sensors 22 may differ significantly from the arrangement of FIG. 2.

The moisture sensors 20 monitor the amount of liquid accumulating on the dense layer 18 below the injection wells 12. If liquid is detected, the amount of steam injected into the landfill 10 is reduced. The temperature sensors 22 monitor the movement of the steam through the trash prism. These sensors 22 provide closer monitoring of the conditions inside the landfill 10 than the moisture sensors 20. The information that they provide about landfill 10 conditions can be used to adjust the amount of steam injected in order to prevent liquid from accumulating on the dense layer 18, rather than adjusting the steam injection after liquid is detected.

Follow-up PPT profiles preferably monitor the decomposition of the organic material and the settlement between the dense layers 18. As the volume of the organic material between the dense layers 18 is reduced, the amount of steam is also reduced. This reduction helps prevent any liquid from accumulating on the dense layers 18.

The initial PPT profile also preferably surveys the elevation of the top deck of the landfill 10. This data enables monitoring of the overall settlement of the landfill 10.

Figure 4:
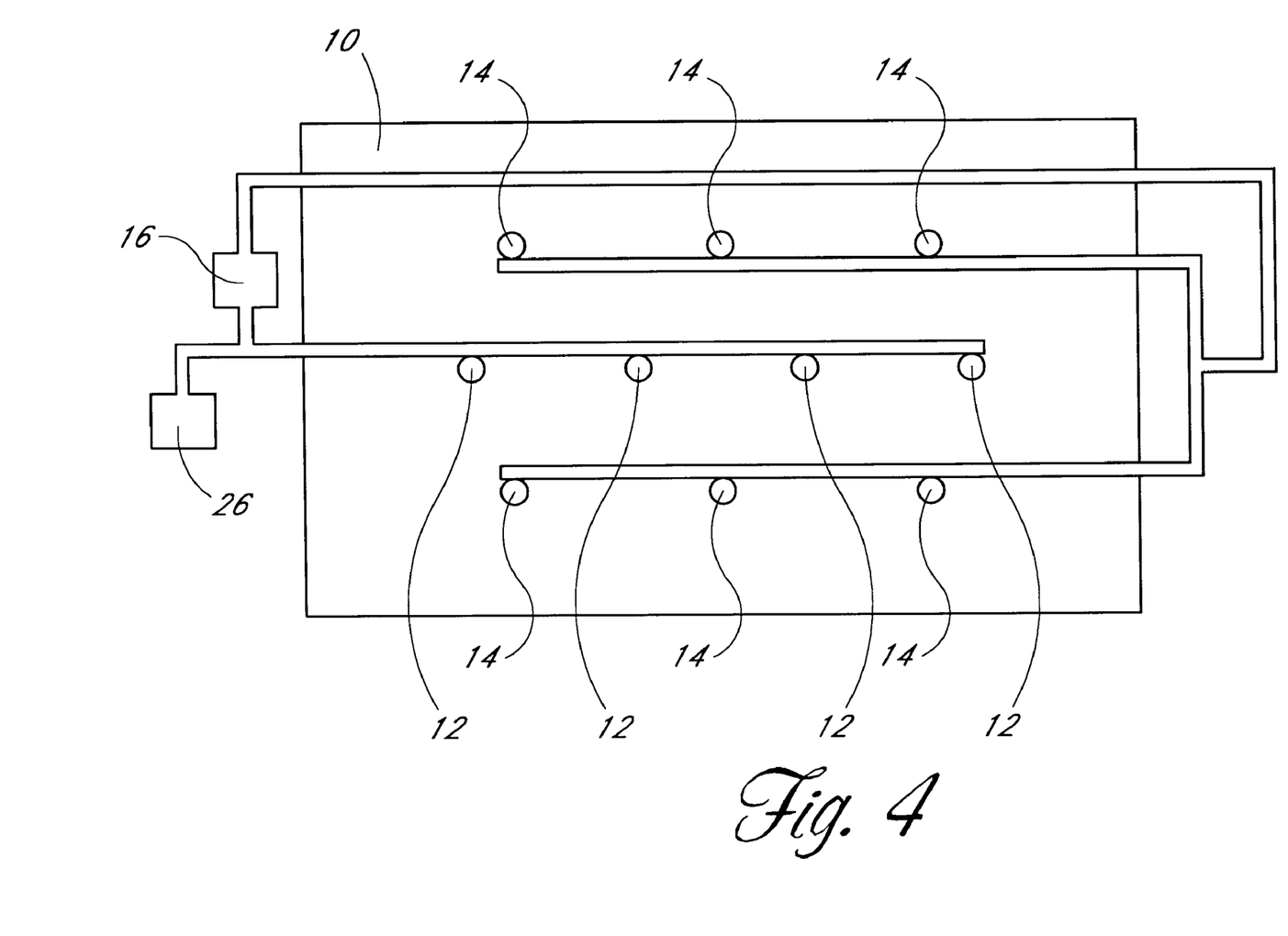
FIG. 4 is a schematic top view of an apparatus for performing another preferred embodiment of the present method.

This method assumes that the landfill 10 is in its anaerobic phase. A method of injecting during the aerobic phase is depicted in FIG. 4. A blower 26 forces air along with the steam into the landfill 10 through the injection wells 12. The collectors 14 create localized low pressure zones, drawing the steam through the landfill 10. Because the landfill 10 is in the aerobic phase, little or no methane is produced by the decomposition of the organic refuse. Thus, rather than collecting methane and transporting it to a storage area, the collectors 14 instead collect steam from the landfill 10 and transport it back to the steam source 16, such as a boiler, heat exchanger or power plant.

Figure 3:
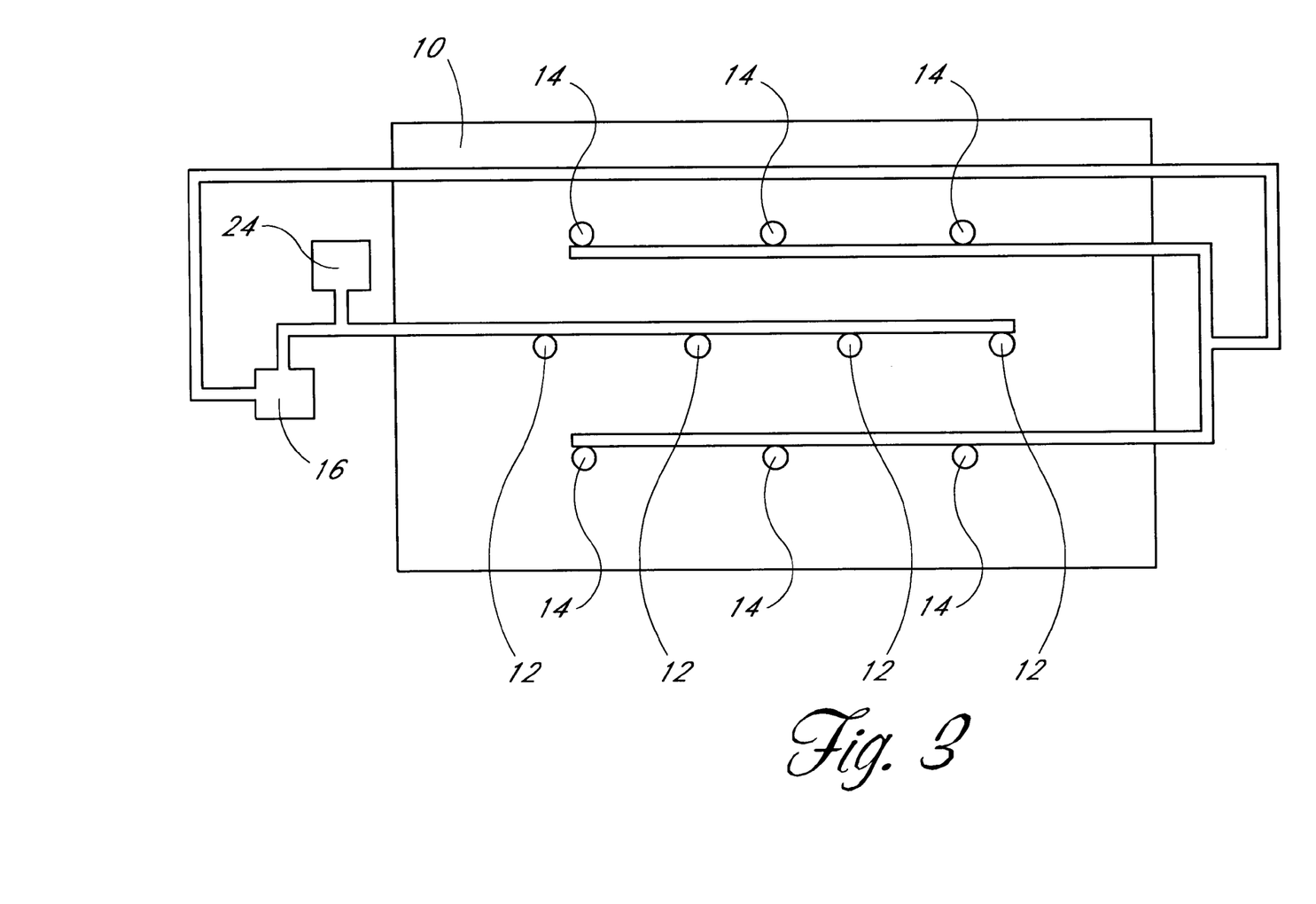
FIG. 3 is a schematic top view of an apparatus for performing another preferred embodiment of the present method.

Another preferred method of injecting steam into a landfill 10 proceeds as in the previous methods, but the steam includes an anaerobic gas fertilizer 24. One or more gaseous fertilizers 24 are preferably introduced into the steam as it emerges from the boiler, heat exchanger, etc, as illustrated in FIG. 3. If the landfill 10 is still in the aerobic phase, the introduction of nitrous oxide assists in depleting the oxygen within the landfill 10, which accelerates the transition to the anaerobic phase. If the landfill 10 is already in the anaerobic phase, the introduction of ammonia and/or ammonia nitrate promotes the growth of anaerobic bacteria, which accelerate the biodegradation of the organic material in the landfill 10.

Another preferred method of injecting steam into a landfill 10 comprises raising the temperature and pressure of the steam following the biodegradation of the organic component of the refuse and the recovery of most of the methane. The temperature is preferably increased to a level sufficient to melt most of the plastic in the landfill 10. However, the plastic is preferably melted without combustion, so that toxic fumes are not produced. With plastic comprising 20% to 30% of the volume of a typical landfill 10, and plastic shrinking to 50% of its original volume upon melting, the temperature increase recovers up to 15% of the volume of the landfill 10.

To increase the pressure within the landfill 10, the valves on the gas collectors 14 are preferably closed. The increased pressure raises the temperature within the landfill 10. When the temperature reaches approximately 400° F. to 600° F. at the midpoint between the injectors 12 and collectors 14, the valves on the gas collectors 14 are preferably opened. The opening creates a pressure gradient that drives the steam toward the gas collectors 14. Steam at this temperature is considered dry. Most of it is recoverable through the collector system prior to condensing inside the landfill 10. The negative consequences of over-saturating the landfill 10 are thus avoided, despite injecting a relatively large amount of steam into the landfill 10.

In another preferred method, the volume of the plastic component of the refuse is reduced before the refuse is placed in a landfill. The refuse is preferably placed in a containerized trammel, into which high-temperature and high-pressure steam is injected as the trammel is rotated. To recycle the plastic, screens are preferably placed inside the trammel so that the plastic sticks to them. To recover the plastic, the screens are removed. According to this method, the organic component of the refuse is thoroughly moisturized by the steam prior to being placed in the landfill. The pre-moisturization further accelerates the bio-degradation of the organic refuse once it is buried in a landfill.

SCOPE OF THE INVENTION

The above presents a description of the best mode contemplated for carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention.

What is claimed is:

1. A method of enhancing methane gas production in a landfill having a trash prism, accelerating decomposition/biodegradation of an organic component of the trash prism, and increasing a rate of settlement of the landfill, comprising the steps of:

providing at least one steam injection well and at least one gas extraction collector;

providing a source of steam;

injecting the steam into the trash prism via the steam injection well; and extracting methane gas produced by decomposition/biodegradation of organic refuse within the trash prism via the gas extraction collector.

2. The method of claim 1, wherein the steam injection well and the gas extraction collector each comprise push-in screens and risers.

3. The method of claim 1, further comprising the step of determining an ideal location for the steam injection well and gas extraction collector using a piezo-penetrometer test profile.

4. The method of claim 1, wherein the steam injection well and the gas extraction collector are installed using a piezo-penetrometer test rig.

5. The method of claim 1, wherein the source of steam comprises a boiler.

6. The method of claim 1, wherein the source of steam comprises a heat exchanger on a gas flare.

7. The method of claim 1, wherein the source of steam comprises exhaust steam from a power plant.

8. The method of claim 1, wherein the source of steam comprises liquid water from a flooded portion of the landfill that is boiled using heat from a submersible heater.

9. The method of claim 1, further comprising the step of injecting a gaseous anaerobic fertilizer into the landfill.

10. The method of claim 9, wherein the gaseous anaerobic fertilizer comprises ammonia.

11. The method of claim 9, wherein the gaseous anaerobic fertilizer comprises ammonia nitrate.

12. The method of claim 1, further comprising the step of injecting nitrous oxide into the landfill.

13. The method of claim 1, further comprising the step of raising a temperature and a pressure of the steam following substantial completion of the biodegradation/decomposition of the organic component of the trash prism and recovery of substantially all of the methane produced thereby.

14. The method of claim 13, wherein the temperature of the steam is raised to approximately 400° F. to 600° F.

15. The method of claim 14, wherein a valve on the gas extraction collector is opened upon the temperature of the steam reaching approximately 400° F. to 600° F. at a midpoint between the steam injection well and the gas extraction collector.

16. The method of claim 14, wherein substantially all of the steam is recovered through the gas extraction collector prior to condensing inside the landfill.

17. The method of claim 1, further comprising the step of placing moisture sensors and temperature sensors within the landfill.

18. The method of claim 17, further comprising the step of monitoring a liquid accumulation on a dense layer below the injection well.

19. The method of claim 18, further comprising the step of reducing an amount of steam injected upon detection of liquid.

20. The method of claim 17, further comprising the step of monitoring movement of the steam through the trash prism using the. temperature sensors.

21. The method of claim 1, further comprising the step of monitoring the biodegradation/decomposition of the organic component of the trash prism and an amount of settling between dense layers using a piezo-penetrometer test profile.

22. The method of claim 21, further comprising the step of reducing an amount of steam injected as a volume of the organic component of the trash prism is reduced.

23. The method of claim 1, further comprising the step of monitoring a rate of settling of the landfill using a top deck elevation measurement from a piezo-penetrometer test profile and a survey of the top deck.

24. The method of claim 1, further comprising the step of monitoring a landfill gas at the gas extraction collector.

25. The method of claim 1, wherein the source of steam is a boiler.

26. The method of claim 25, wherein the methane extracted from the landfill is used to fire the boiler.

27. The method of claim 1, wherein the source of steam is a heat exchanger.

28. The method of claim 1, wherein the source of steam is exhaust steam from a power plant.

29. A method of accelerating decomposition/biodegradation of an organic component of a landfill having a trash prism, and increasing a rate of settlement of the landfill, comprising the steps of:

providing at least one air injection well and at least one gas extraction collector;

providing a source of steam;

injecting air and the steam into the trash prism via the air injection well; and collecting the steam via the gas extraction collector.

30. The method of claim 29, wherein the steam replaces moisture in the landfill that is lost during aerobic degradation.

31. The method of claim 30, wherein a pipe connected to the gas extraction collector transports the steam to another location.

32. The method of claim 31, wherein the steam is transported back to the source of stream.

* * * * *